United States Patent
Nakanishi et al.

(10) Patent No.: US 6,660,281 B1
(45) Date of Patent: *Dec. 9, 2003

(54) SILICONES FOR POWER TREATMENT POWERS HAVING SURFACE TREATED WITH SAID SILICONES AND COSMETIC MATERIALS CONTAINING SAID POWERS

(75) Inventors: Tetsuo Nakanishi, Gunma-Ken (JP); Koji Sakuta, Gunma-Ken (JP); Ichiro Ono, Gunma-Ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/606,017

(22) Filed: Jun. 29, 2000

(30) Foreign Application Priority Data

Jun. 30, 1999 (JP) ............................ 11/186201
Jun. 21, 2000 (JP) ........................ 2000/185999

(51) Int. Cl.⁷ ............................ A61K 6/00; A61K 7/00; A61K 31/74; A61K 47/48; A01N 55/00
(52) U.S. Cl. ................. 424/401; 424/78.02; 424/78.17; 514/63; 514/772.1; 556/400
(58) Field of Search ........................ 424/401, 67, 69, 424/70.12, 78.02, 78.17; 514/723, 724, 772.1, 63; 556/400

(56) References Cited

U.S. PATENT DOCUMENTS

| | | | |
|---|---|---|---|
| 4,631,208 A | | 12/1986 | Westall |
| 4,832,944 A | | 5/1989 | Socci et al. |
| 5,310,842 A | | 5/1994 | Ichinohe et al. |
| 5,358,719 A | * | 10/1994 | Mellul et al. ............... 424/497 |
| 5,557,000 A | | 9/1996 | Minemura |
| 5,851,539 A | * | 12/1998 | Mellul et al. ............... 424/401 |
| 5,880,210 A | * | 3/1999 | Schulz et al. ............... 524/731 |
| 5,902,569 A | * | 5/1999 | Oshima et al. ............... 424/59 |
| 6,037,407 A | * | 3/2000 | Derian et al. ............... 524/837 |
| 6,132,743 A | * | 10/2000 | Kuroda et al. ............... 424/401 |

FOREIGN PATENT DOCUMENTS

| | | | |
|---|---|---|---|
| EP | 0 545 022 A1 | * | 8/1992 |
| EP | 0 665 277 | | 2/1995 |
| WO | 9951192 | * | 1/1999 |

* cited by examiner

*Primary Examiner*—Sreeni Padmanabhan
*Assistant Examiner*—Lauren Q. Wells
(74) *Attorney, Agent, or Firm*—Millen, White, Zelano & Branigan, P.C.

(57) ABSTRACT

Powders treated with silicones represented by the following formula (1):

$$R^1_a R^2_b R^3_c SiO_{(4-a-b-c)/2} \quad (1)$$

wherein
$R^1$, $R^2$, $R^3$ a, b and c are as defined herein, are suitable for use in cosmetic materials.

41 Claims, No Drawings

SILICONES FOR POWER TREATMENT POWERS HAVING SURFACE TREATED WITH SAID SILICONES AND COSMETIC MATERIALS CONTAINING SAID POWERS

FIELD OF THE INVENTION

The present invention relates to novel silicones for powder treatment, powders having the surface treated with such silicones, and cosmetic materials containing such surface-treated powders. More specifically, the invention is concerned with silicones that are used for surface treatment of powders to provide the treated powders with high affinity for general fats and oils, such as ester oils and glycerides, silicone oils and fluorinated oils, and further with cosmetic materials which contain the powders having the surface treated with the aforesaid silicones to acquire excellent dispersibility and stable emulsion state and ensure a dry feel for the users.

BACKGROUND OF THE INVENTION

In general the makeup is smeared with secretion from humans, such as sweat, tear and sebum. In particular, the leading cause of the makeup spoilage consists in that the powder in a cosmetic material is wetted excessively by the sebum secreted from the skin in addition to oil ingredients compounded in the cosmetic material. Therefore, with the intention of reducing the oil ingredients remaining on the skin after the makeup is done, it has been attempted to use volatile oils, such as octamethylcyclotetrasiloxane and decamethylcyclopentasiloxane, as a part of the oil ingredients compounded in a cosmetic material.

Further, the rub and the water given to the makeup constitute external factors inhibiting the makeup effect from lasting long. For the purpose of preventing the makeup from coming off by contact with aqueous substances, such as sweat and tears, or maintaining the skin protecting effect by preventing a loss of water-soluble components and sebum in the skin, it has been carried out to heighten the water repellency by mixing a silicone oil in the cosmetic material. In recent years, the silicone oils, represented, e.g., by dimethylpolysiloxanes, have been prevailingly used as an oil ingredient for cosmetic materials because of their characteristics, including light feel, excellent water repellency and high safety.

On the other hand, the pigments represented by ferric oxide red and titanium dioxide, and powders such as mica and sericite are widely used in the field of cosmetics, including nail color, nail coat, face powder, mascara and eye liner. In using these powders for cosmetics, the powder surface is generally subjected to treatment with metal soap, alumina, silica or phosphoric acid for the purpose of imparting sufficient water repellency and safety to the powders.

For instance, the method of using 12 to 60 parts by weight of methylhydrogenpolysiloxanes per 100 parts by weight of powders to effect surface treatment of the powders is disclosed in Japanese Patent 2,719,303, and the method of using the straight-chain silicone having one alkoxy-modified end for surface treatment of powders is disclosed in Japanese Tokkai Hei 7-196946 (the term "Tokkai" as used herein means an "unexamined published patent application"). Although the powder treatment with silicones is a generally known art, it has been desired to develop special silicones capable of ensuring further improvements in compatibility between the treated powders and general oils, fluorinated oils or silicone oils, and besides, enhanced stability in emulsions containing both treated powders and those oils.

SUMMARY OF THE INVENTION

As a result of our intensive studies aiming at developing cosmetic materials having a light feel, sufficiently high water repellency and a makeup effect of long-duration, it has been found that the powders treated with one-end reactive silicone-grafted silicone compounds have extremely high water repellency, sufficient dispersibility in volatile oils, such as octamethylcyclotetrasiloxane and decamethylcyclopentasiloxane, and good usability as powders for cosmetic materials, and besides, the cosmetic materials using them have a light feel, thereby achieving the present invention.

Therefore, a first object of the invention is to provide a powder-treating agent which has good affinity for fats and oils used in general cosmetic materials and can impart excellent capability for emulsification to the powder.

A second object of the invention is to provide a powder having good affinity for fats and oils used in general cosmetic materials and high capability for emulsification.

A third object of the invention is to provide a cosmetic material having excellent storage stability in an emulsified condition.

The above-described objects are attained with silicones represented by the following formula (1) as a powder-treating agent, a powder treated with the aforesaid silicones, and a cosmetic material containing the aforesaid powder:

$$R^1_a R^2_b R^3_c SiO_{(4-a-b-c)/2} \quad (1)$$

wherein $R^1$ groups, which are the same or different, each represent an organic group selected from the class consisting of alkyl groups containing 1 to 30 carbon atoms, aryl groups, aralkyl groups, fluorinated alkyl groups and organic groups represented by the following formula (2); $R^2$ groups each represent a reactive substituent selected from the class consisting of a hydrogen atom, a hydroxyl group and alkoxy groups containing 1 to 6 carbon atoms, which is attached to a silicon atom in the siloxane chain directly or via a linkage group comprising at least one carbon, oxygen or silicon atom; $R^3$ groups each represent a silicone compound residue represented by the following formula (3); a is a number of from 1.0 to 2.5; b is a number of from 0.001 to 1.5; and c is a number of from 0.001 to 1.5

(2)

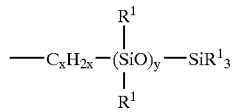

(3)

wherein $R^4$ is a hydrocarbon group containing 4 to 30 carbon atoms or an organic group represented by $R^5$—(CO)—; $R^5$ is a hydrocarbon group containing 1 to 30 carbon atoms; d is an integer of from 0 to 15, e is an integer of from 0 to 50, and f is an integer of from 0 to 50; and x is an integer of from 1 to 5, and y is an integer of from 0 to 500.

The powders surface-treated with the aforementioned silicones have good affinity for oils generally used in cosmetic materials, such as other silicone oils, ester oils and hydrocarbon oils, and so they have excellent capability for emulsification. Therefore, the emulsions using the powders surface-treated with the present silicones have excellent storage stability, and so they can be effectively applied to cosmetic materials.

DETAILED DESCRIPTION OF THE INVENTION

As described above, the present silicone compounds are represented by formula $R^1{}_aR^2{}_bR^3{}_c SiO_{(4-a-b-c)/2}$ (referred to as formula (1)).

Each $R^1$ group in formula (1) represents an organic group selected from the class consisting of 1–30C alkyl groups, aryl groups, aralkyl groups, fluorinated alkyl groups and organic groups represented by $—C_dH_{2d}—O—(C_2H_4O)_e(C_3H_6O)_fR^4$ (which is referred to as formula (2)), wherein d, e and f are each an integer and fall within the following ranges: $0 \leq d \leq 15$, $0 \leq e \leq 50$, $0 \leq f \leq 50$; $R^4$ represents a 4–30C hydrocarbon group or an acyl group represented by $R^5—(CO)—$; and $R^5$ represents a 1–30C hydrocarbon group.

Examples of an alkyl group as $R^1$ include a methyl group, an ethyl group, a propyl group, a butyl group, a pentyl group, a hexyl group, a heptyl group, an octyl group, a nonyl group and a decyl group; those of a cycloalkyl group as $R^1$ include a cyclopentyl group and a cyclohexyl group; those of an aryl group as $R^1$ include a phenyl group and a tolyl group; those of an aralkyl group as $R^1$ include a benzyl group and a phenetyl group; and those of a fluorinated alkyl group as $R^1$ include a trifluoropropyl group and a heptadecafluorodecyl group.

In addition, examples of an organic group represented by formula (2) include higher alcohol residues, such as residues of higher alcohols, such as cetyl alcohol, oleyl alcohol and stearyl alcohol, and polyoxyalkylene adducts thereof; higher alcohol alkenyl ether residues, and polyoxyalkylene adducts thereof; higher fatty acid residues, such as residues of oleic acid, stearic acid and behenic acid, and polyoxyalkylene adducts thereof; and higher fatty acid alkenyl ester residues and polyoxyalkylene adducts thereof.

More specifically, the formula (2) is $—O—(C_2H_4O)_e(C_3H_6O)_fR^3$ when d is 0. Further, it becomes $—O—R^3$ in the case of e=0 and f=0, and represents a residue of higher alcohol such as cetyl alcohol, oleyl alcohol or stearyl alcohol, or a residue of higher fatty acid such as oleic acid, stearic acid or behenic acid. In a case of e,f$\geq$1, on the other hand, the formula (2) represents an alcohol residue of higher alcohol/alkylene oxide adduct (having OH at the end).

When d is 1 or 2 the formula (2) is $—C_dH_{2d}—O—(C_2H_4O)_e(C_3H_6O)_fR^3$ and this group is formed by dehydrohalogenation reaction between Si—OH group and $X(CH_2)_n—O—(C_2H_4O)_e(C_3H_6O)_fR^3$ (wherein X is halogen).

The $—C_dH_{2d}—O—(C_2H_4O)_e(C_3H_6O)_fR^3$ group in the case of d$\geq$3 is a group introduced by the addition reaction between Si—H and a higher alcohol alkenyl ether or a fatty acid alkenyl ester, or a polyalkylene oxide adduct thereof.

$R^2$ groups are each a reactive substituent selected from the class consisting of a hydrogen atom, a hydroxyl group and alkoxy groups containing 1 to 6 carbon atoms such as methoxy, ethoxy and isopropoxy groups. And this reactive substituent is attached to a silicon atom in the siloxane chain directly or via a linkage group comprising at least carbon, oxygen or silicon atom, such as an alkylene group or an alkylene ether linkage. For instance, such reactive substituents can be introduced into the present compounds by addition reaction between SiH groups and vinyltrichlorosilane, vinyltris (β-methoxyethoxy)silane, vinyltrimethoxysilane or vinyltriethoxysilane.

In the case of using silicone compounds for cosmetics, the evolution of methanol and hydrogen gas caused by methoxy groups and SiH groups remaining unreacted becomes a problem. Therefore, the desirable reactive substituent is a hydroxyl or ethoxy group. Such a reactive substituent may be a monofunctional, difunctional or trifunctional group, with examples including dimethylethoxysilyl, diethoxymethylsilyl and triethoxysilyl groups.

$R^3$ groups are each a silicone compound residue represented by the following formula (3):

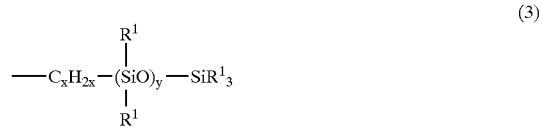

wherein x is an integer of from 1 to 5, and y is an integer of from 0 to 500, preferably from 3 to 100. For instance, x has a value of 2 when the silicone compound residue of formula (3) is introduced by the reaction between a vinyl group and hydrogensiloxane. When the integer "y" in $R^3$ has a value greater than 500, the resultant $R^3$ group tends to cause a problem of lowering the reactivity in the introduction into the hydrogensiloxane constituting the main chain.

"a" in formula (1) is a number of from 1.0 to 2.5, preferably from 1.2 to 2.3, and "b" in formula (1) is a number of from 0.001 to 1.5, preferably from 0.05 to 1.0. When b is smaller than 0.001, the reactivity of such a silicone with powders is low. "c" in formula (1) is a number of from 0.001 to 1.5, preferably from 0.05 to 1.0. When these requirements are fulfilled, the compatibility of the present silicones with general silicone oils can be fully achieved.

When the present silicone compounds represented by formula (1) are used as a powder surface-treating agent, the weight average molecular weight suitable therefor, though it has no particular limits, is from 300 to 100,000. When the silicone compound of formula (1) has a weight average molecular weight higher than 100,000, it has a sticky feel because of its high viscosity; while, when the silicone compound has a weight average molecular weight lower than 300, it cannot provide smooth texture which is a characteristic of silicones. In particular, it is desirable for the present silicone compounds to have their weight average molecular weight in the range of 1,000 to 10,000.

The present silicone compounds represented by formula (1) can be synthesized with ease by addition reaction between organohydrogenpolysiloxanes and silicone compounds represented by the following general formula (4) and, if desired, alkene compounds as well in the presence of a platinum or rhodium catalyst:

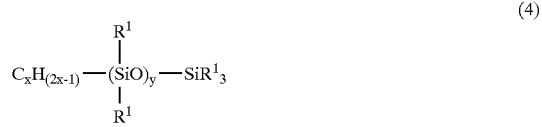

wherein $R^1$, x and y have the same meanings as in formula (3) respectively.

The organohydrogenpolysiloxanes used therein may have a straight-chain structure or a cyclic structure. However, the straight-chain organohydrogenpolysiloxanes are preferable because they have better addition reactivity. Additionally, the organohydrogen polysiloxanes have no particular restriction as to the bonding site of SiH group(s), but the SiH group(s) may be situated in side chain(s) or at the molecular end(s).

The mixing ratio of the organohydrogenpolysiloxanes to the combination of the silicone compound of formula (4) and the alkene compound can be from 0.2 to 2.0, expressed in terms of the quantity by mole of the terminal unsaturated group per mole of SiH groups. Preferably, the foregoing ratio is adjusted to the range of 0.5 to 1.2 in order to avoid the evolution of hydrogen gas caused by the SiH groups remaining unreacted.

The foregoing addition reaction is carried out effectively in the presence of a platinum catalyst or a rhodium catalyst. Suitable examples of such a catalyst include chloroplatinic acid, alcohol-modified platinic chloride and platinic chloride-vinylsiloxane complex.

The amount of catalyst used, though it may be a conventional catalytic amount, is desirably at most 500 ppm, particularly desirably at most 20 ppm, based on the platinum or the rhodium. The addition reaction may be carried out in an organic solvent, if needed. Examples of an organic solvent usable therein include aliphatic alcohols, such as methanol, ethanol, 2-propanol and butanol; aromatic hydrocarbons, such as toluene and xylene; aliphatic or alicyclic hydrocarbons, such as n-pentane, n-hexane and cyclohexane; and halogenated hydrocarbons, such as dichloromethane, chloroform and carbon tetrachloride.

The addition reaction has no particular restriction as to its reaction conditions. However, it is desirable that the addition reaction be-performed for 1 to 10 hours under reflux.

The present silicone compounds can be used for various purposes. In particular, they are suitable for treatment of powder surface. In this case, the appropriate proportion of the silicone compound represented by formula (1) mixed with a powder is from 0.1 to 30 parts by weight, preferably from 0.5 to 10 parts by weight, per 100 parts by weight of the powder.

The present silicone compounds are applicable to surface treatment of any powders so far as the powders can be used in general cosmetic materials, irrespective of their shape (whether it is spherical, acicular or tabular), their size (whether it is on the order of fume, fine grain or pigment), and their structure (whether it is porous or nonporous) Examples of powders usable in the invention include inorganic powders (including white pigments and extender pigments), organic powders, surfactant metal salt powders, colored pigments, pearl pigments, metallic powder pigments and natural colors. Of these powders, white pigments, such as zinc oxide and titanium dioxide, and extender pigments, such as mica and sericite, are especially suitable for the treatment with the present silicones.

The present silicone compounds as powder-treating agents can achieve the powder-surface treatment in accordance with any of known methods. For instance, the method applied to the present treatment can be selected properly from the following methods:

1. A method of dispersing the desired powder into a treating agent-mixed water or organic solvent to treat the powder surface.

2. A method of mixing a powder with a powder-treating agent and then grinding the resulting mixture with a grinder, such as a ball mill or a jet mill, to treat the powder surface.

3. A method of mixing a silicone oil (especially methylhydrogenpolysiloxanes or methylhydroxypolysiloxanes) with a solvent, dispersing a powder into the resultant mixture to adsorb the silicone oil to the powder surface and then drying the resulting powder so as to cause sintering.

The powder whose surface is treated with the present silicone compound can be mixed in a cosmetic material in a proportion of from about 0.1 to about 99 weight %, although the suitable proportion depends on the type and the state of the cosmetic material.

The cosmetic materials in which the powders treated with the present silicone compounds are incorporated (which are referred to as "the present cosmetic materials") can further contain oils depending on the desired purposes thereof. In the present cosmetic materials, any unctuous agents can be used whether they are ina solid, semisolid or liquid state, provided that they have so far been used for general cosmetics.

More specifically, not only natural animal and vegetable fats and oils but also semi-synthetic fats and oils can be mixed in the present cosmetic materials, with examples including avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice branoil, sugarcanewax, sasanquaoil, saffloweroil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, beeds wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil. Additionally, the term "POE" as used herein stands for polyoxyethylene.

Examples of hydrocarbon oil which can be mixed therein include ozokerite, squalane, squalene, ceresine, paraffin, paraffin wax, liquid paraffin, pristane, polyisobutylene, microcrystalline wax and Vaseline; and those of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of a higher alcohol which can be mixed therein include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oil which can be mixed therein include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester and diisostearyl malic acid; and examples of glyceride oil which can be mixed therein include acetoglyceride, triisooctanoic acid glyceride, triisostearic acid glyceride, triisopalmitic acid glyceride, tri-2-ethylhexanoic acid glyceride, monostearic acid glyceride, di-2-heptylundecanoic acid glyceride, trimyristic acid glyceride and myristic acid isostearic acid diglyceride.

As examples of a silicone oil which can be mixed, mention may be made of organopolysiloxanes having from low to high viscosities, such as dimethylpolysiloxane, methylphenylpolysiloxane, methylhydrogenpolysiloxane and a copolymer of dimethylsiloxane and methylphenylsiloxane; cyclic siloxanes, such as octamethylcyclotetrasiloxane, decamethylcyclopentasiloxane, dodecamethylcyclohexasiloxane, tetramethyltetrahydrogencyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, amino-modified silicones, fluorine-modified silicones, and solutions of silicone resin.

As examples of fluorine-containing oil which can be mixed, mention may be made of perfluoropolyether, perfluorodecalin and perfluorooctane.

Furthermore, the present cosmetic materials can contain one or more of a surfactant, if desired. The surfactant contained therein has no particular restriction, but it may be any of anionic, cationic, nonionic and amphoteric ones so long as they have hitherto been used in general cosmetics. In particular, the surfactants having their HLB values in the range of 2 to 8 are suitable for the present cosmetic materials.

Examples of a usable anionic surfactant include fatty acid soap, such as sodium stearate or triethanolamine palmitate; alkyl ether carboxylic acids and salts thereof; salts of amino acid-fatty acid condensates; alkanesulfonates; alkenesulfonates; sulfonated fatty acid esters; sulfonated fatty acid amides; sulfonates of formaldehyde condensate type; alkylsulfates; higher secondary alcohol sulfates; alkyl and aryl ether sulfates; fatty acid ether sulfates, fatty acid alkylolamide sulfates; ether sulfates, such as Turkeky red oil; alkyl phosphates; ether phosphates; alkyl aryl ether phosphates; amide phosphates; and active agents of N-acylamino acid type.

Examples of a usable cationic surfactant include amine salts, such as alkylamie salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ehter, polyoxyethylene phytosterol ether, polyoxyethylene cholestanol ether, polyoxyethylene cholesteryl ether, polyoxyalkylene-modified organopolysiloxanes, organopolysiloxanes modified with both polyoxyalkylene and alkyl groups, alkanolamides, sugar ethers and sugar amides; and examples of a usable amphoteric surfactant include betaine, aminocarboxylates and imdazoline derivatives.

In the present cosmetic materials, another powder can further be used depending on the desired purposes. Such a powder is not particularly restricted as to its shape (whether it is spherical, acicular or tabular), its size (whether it is on the order of fume, fine grain or pigment), and its structure (whether it is porous or nonporous), provided that it has so farbeenusedin conventional cosmetic materials. For instance, inorganic powders, organic powders, surfactant metal salt powders, colored pigments, pearl pigments, metallic powder pigments and natural colors can be used in the present cosmetic materials, if desired.

Examples of a usable inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxie, boron nitride and silica.

Examples of a usable organic powder include polyamide powder, polyester powder, polyethylene powder, polypropylene powder, polystyrene powder, polyurethane powder, benzoguanamine powder, polymethylbenzoguanamine powder, polytetrafluoroethylene powder, polymethylmethacrylate powder, cellulose powder, silk powder, nylon powder such as 12-nylon powder or 6-nylon powder, silicone powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder, polycarbonate resin powder, microcrystalline fiber powder, starch powder and lauroyl lysine powder.

Examples of a usable surfactant metal salt powder (metal soap powder) include powders of zinc stearate, aluminum stearate, calcium stearate, magnesium stearate, zinc myristate, magensium myristate, zinc cetylphosphate, calcium cetylphosphate and zinc sodium cetylphosphate.

Examples of a usable colored pigment include inorganic red pigments, such as iron oxide, iron hydroxide and iron titanate; inorganic brown pigments, such as γiron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments as recited above.

Examples of a usable pearl pigment include titanium oxide-coated mica, bismuth oxychloride, titanium oxide-coated bismuth oxychloride, titanium oxide-coated talc, fish scales, and titanium oxide-coated colored mica; and examples of a usable metallic powder pigment include aluminum powder, copper powder and stainless powder.

Examples of a usable tar pigment include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207 (according to the pigment nomenclature method in JIS); and examples of a usable natural pigment include powders of carminic acid, laccaic acid, carthamin, bradilin and crocin.

Additionally, complexes of the powders as recited above or those obtained by treating the powders as recited above with general oil, a silicone oil other than the present silicone compounds, a fluorine-containing compound or a surfactant may be used. Also, these powders may be used as a mixture of two or more thereof, if desired.

In the present cosmetic materials, the compounds having at least one alcoholic hydroxyl group per molecule can be used depending on the desired purposes of the cosmetic materials.

Examples of alcohols which can be added include lower alcohols, such as ethanol and isopropanol; sugar alcohols, such as sorbitol and maltose; and sterols, such as cholesterol, sitosterol, phytosterol and lanosterol.

Examples of water-soluble polymers which can be added include vegetable polymers, such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride.

In these water-soluble polymers, film-forming agents, such as polyvinyl alcohol and polyvinyl pyrrolidine, are also included.

The present cosmetic materials can further contain one or more kinds of cross-linked organopolysiloxanes depending on their respectively desired purposes.

The cross-linked organopolysiloxanes suitable for the present cosmetic materials are those which cause swelling when they contain a silicone having low viscosity of from 0.65 to 10.0 mm$^2$/sec (25°) in a quantity larger than their self weight. Further, it is desirable that the cross-linked structure of those organopolysiloxanes be formed by the reaction between the hydrogen atoms bonded directly to silicon atoms and a cross-linking agent having at least two vinylic reactive moieties per molecule. Furthermore, it is desirable in the foregoing reaction to use the cross-linking agent containing at least one moiety selected from polyoxyalkylene, alkyl, alkenyl, aryl and fluoroalkyl moieties. The suitable proportion of such cross-linked organopolysiloxanes mixed in a cosmetic material according to the invention is from 0.1 to 30 weight %, preferably from 1.0 to 10 weight %, to the total weight of the cosmetic material.

The present cosmetic materials can further contain one or more kinds of silicone resins, such as acryl-silicone graft or block copolymers and silicone compounds having network structure, if needed.

In particular, acrylsilicone resins are suitable for the present cosmetic materials. Further, it is desirable that at least one moiety selected from the group consisting of pyrrolidone, long-chain alkyl, polyoxyalkylene and fluoroalkyl moieties be present in such an acrylsilicone resin molecule. The other favorable silicone resins are silicone compounds having network structure. When the silicone resins, such as acryl-silicone graft or block copolymer and silicone compounds having network structure, are mixed in the present cosmetic material, the appropriate proportion of silicone resins mixed is from 0.1 to 20 weight %, preferably from 1 to 10 weight %, to the total weight of the cosmetic material.

To the present cosmetic materials, the ingredients used in general cosmetic materials, such as oil-soluble gelling agents, clay minerals modified with organic compounds, resins, ultraviolet absorbents, moisture-holding agents, antiseptics,. antimicrobial agents, perfume, salts, antioxidants, pH regulators, chelating agents, refrigerant, anti-inflammatory agents, skin beautifying components (a skin whitener, a cell activator, a rough dry skin improver, a blood circulation promoter, a skin astringent and an antiseborrheic agent), vitamins, amino acids, nucleic acids, hormones and clathrate compounds, can be added so far as they have no adverse influence on the effects of the present invention.

Examples of an oil-soluble gelling agent which can be added include metal soaps, such as aluminum stearate, magnesium stearate and zinc myristate; amino acid derivatives, such as N-lauroyl-L-glutamic acid and $\alpha,\gamma$-di-n-butylamine; dextrin fattyacidesters, such as dextrinpalmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of an ultraviolet absorbent which can be added include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane.

Examples of a moisture-holding agent which can be added include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylic acid, polyoxyethylene glycoside, and polyoxypropylene methylglycoside.

Examples of an antiseptic agent which can be added include alkyl p-hydroxybenzoates, benzoic acid, sodium benzoate, sorbic acid, potassium sorbate and phenoxyethanol; and those of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitizer and phenoxyethanol.

Examples of an antioxidant which can be added include tocopherol, butylhydroxyanisole, dibutylhydroxytoluene and phytic acid; those of a pH regulator which can be added include lactic acid, citric acid, glycolic acid, succinic acid, tartaric acid, dl-malic acid, potassium carbonate, sodium hydrogen carbonate and ammonium hydrogen carbonate; those of a chelating agent which can be added include alanine, sodium ethylenediaminetetraacetate, sodium polyphosphate, sodium metaphosphate and phosphoric acid; those of a refrigerant which can be added include L-menthol and camphor; and those of an anti-inflammatory agent which can added include allantoin, glycyrrhizin and salts thereof, glycyrrhetinic acid and stearyl glycyrrhetinate, tranexamic acid and azulene.

Examples of a skin-beautifying component which can be added include whitening agents, such as placenta extract, arbutin, glutathione and Yukinoshita extract; cell activators, such as royal jelly, photosensitizer, cholesterol derivatives and calf blood extract; rough dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and anti-seborrheic agents, such as sulfur and thianthol.

Examples of vitamins which can be added include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbic acid dipalmitic ester, sodium (L-ascorbic acid) -2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an amino acid which can be added include glycine, valine, leucine, isoleucine, serine, threonine, phenylaranine, alginine, lysine, aspartic acid, aspartic acid, glutamic acid, cystine, cysteine, methionine, and tryptophan; those of a nucleic acid which can be added include deoxyribonucleic acid; and those of hormone which can be added include estradiol and ethenyl estradiol.

The term "cosmetic material" as used herein are intended to include skin care products, such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse and treatment. Additionally, the present cosmetic material may have any of forms, including liquid, emulsion, solid, paste, gel and spray forms, if desired.

The present invention will now be illustrated in greater detail by reference to the following examples and comparative examples. However, the invention should not be construed as being limited to these examples. And the term "%" used hereinafter means "% by weight" unless noted otherwise.

Additionally, the entire disclosure of all applications, patents and publications, cited above and below, and of corresponding Japanese applications No. 11-186201, filed on Jun. 30, 1999, and 2000-169265, filed on Jun. 21, 2000, is hereby incorporated by reference.

EXAMPLE 1

Synthesis of Silicone 1

In a reaction vessel were placed 600 parts by weight of organohydrogensiloxanes represented by the following average structural formula (5) and 800 parts by weight of toluene, and thereto 2 parts by weight of a 0.5% toluene solution of chloroplatinic acid was added:

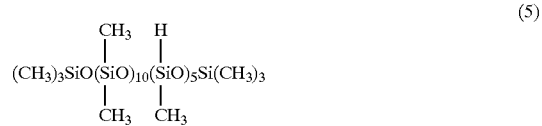

(5)

Then, 1,490 parts by weight of an organopolysiloxane represented by the following structural formula (6) was added dropwise to the reaction vessel:

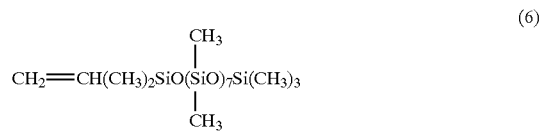

(6)

Further, the reaction was continued for 6 hours under reflux of the solvent while dripping 110 parts by weight of vinyltriethoxysilane into the reaction vessel.

Then, the reaction mixture was heated under reduced pressure to distill off the solvent therefrom. Thus, organopolysiloxanes having the following average structural formula (7) were obtained:

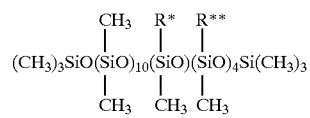

Therein, —R* represents —$C_2H_4Si(OEt)_3$ and —R** represents

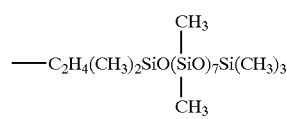

The product obtained was colorless transparent liquid, and it had a viscosity of 57 mm²/s (at 25° C.) and a specific gravity of 0.958 (at 25° C.).

EXAMPLE 2

Synthesis of Silicone 2

After 416 parts by weight of organohydrogensiloxanes represented by the following average structural formula (8) and 400 parts by weight of toluene were placed in a reaction vessel, 2 parts by weight of a 0.5% toluene solution of chloroplatinic acid was added thereto:

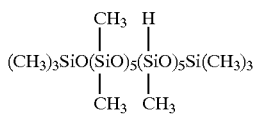
(8)

Then, the mixture of 676 parts by weight of organopolysiloxanes having the foregoing average structural formula (5) with 168 parts by weight of 1-dodecene was added dropwise to the reaction vessel. Further, the reaction was continued for 6 hours under reflux of the solvent while dripping 100 parts by weight of vinyltriethoxysilane into the reaction vessel.

Then, the reaction mixture was heated under reduced pressure to distill off the solvent therefrom. Thus, organopolysiloxanes having the following average structural formula (9) were obtained:

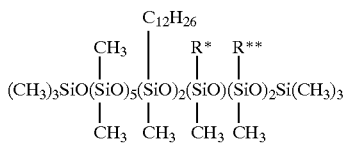
(9)

The product obtained was colorless transparent liquid, and it had a viscosity of 48 mm$^2$/s (at 25° C.) and a specific gravity of 0.951 (at 25° C.).

EXAMPLE 3

Synthesis of Silicone 3

After 608 parts by weight of organohydrogensiloxanes represented by the following average structural formula (10) and 360 parts by weight of toluene were placed in a reaction vessel, 0.2 parts by weight of a 2% toluene solution of chloroplatinic acid was added thereto:

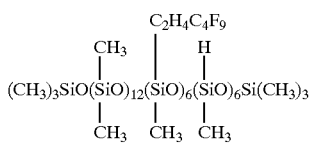
(10)

Further thereto, 740 parts by weight of the organopolysiloxane represented by the foregoing formula (6) was added dropwise under reflux to undergo reaction. Furthermore, the reaction was continued for 6 hours under reflux of the solvent while dripping 45 parts by weight of vinyltriethoxysilane into the reaction vessel. Then, the reaction mixture was heated under reduced pressure to distill off the solvent therefrom. Thus, organopolysiloxanes having the following average structural formula (11) were obtained:

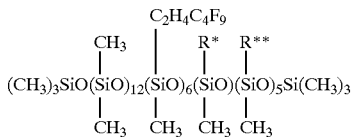
(11)

The product obtained was colorless transparent liquid, and it had a viscosity of 63 mm$^2$/s (at 25° C.) and a specific gravity of 1.053 (at 25° C.).

EXAMPLE 4

Synthesis of Silicone 4

After 600 parts by weight of organopolysiloxanes represented by the foregoing average structural formula (5) and 400 parts by weight of toluene were placed in a reaction vessel, and thereto 2 parts by weight of a 0.5% toluene solution of chloroplatinic acid was added. Thereto, 1,100 parts by weight of organopolysiloxane represented by the foregoing formula (6) was further added dropwise to undergo reaction. Furthermore, 280 parts by weight of polypropylene glycol oleyl allyl ether, RG-1252 (trade name, a product of SANYO CHEMICAL INDUSTRIES, LTD.), was added to the foregoing reaction mixture, and heated for 3 hours under reflux to complete the reaction.

Then, while dripping 110 parts by weight of vinyltriethoxysilane into the reaction vessel, the reaction was further continued for 6 hours under reflux of the solvent. In addition, the reaction mixture was heated under reduced pressure to distill off the solvent therefrom. Thus, organopolysiloxanes having the following average structural formula (12) were obtained:

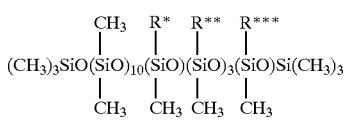
(12)

R*** = ──C$_3$H$_6$O(C$_3$H$_6$O)$_3$C$_{18}$H$_{35}$

The product obtained was colorless transparent liquid, and it had a viscosity of 61 mm$^2$/s (at 25° C.) and a specific gravity of 0.955 (at 25° C.).

EXAMPLES 5 TO 6 AND COMPARATIVE EXAMPLES 1 TO 2

Powder Treated with Silicone

Fine-grained titanium dioxide powder and sericite powder were employed as powders to be treated, and the silicone employed for treating each of these powders was Silicone 1 synthesized in Example 1, Silicone 2 synthesized in Example 2, methylhydrogenpolysiloxane, KF99 (trade name, a product of Shin-Etsu Chemical Co., Ltd.), or alkoxy-modified silicone having the following formula:

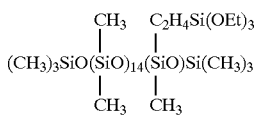

In the treatment, each powder and each silicone were used in the proportion of 98:2 by weight.

Each powder was thermally treated in advance by drying under reduced pressure, and placed in a reaction vessel. Thereto, one of the foregoing silicones diluted with toluene was added gradually with stirring. Then, the temperature of the reaction vessel was raised to distill off the toluene. Further, the stirring was continued for 3 hours at 150° C. to effect the baking treatment. The thus treated powders were each cooled to room temperature in a stream of nitrogen.

The thus treated powders were used for preparing cosmetic material samples.

Specifically, compressed face powder samples were made using the following ingredients in accordance with the process described below:

| Ingredients | Amount mixed (parts by weight) |
|---|---|
| 1. Silicone-treated titanium dioxide | 12.0 |
| 2. Silicone-treated sericite | 35.0 |
| 3. Lecithin-treated talc | 35.1 |
| 4. Lecithin-treated spherical nylon powder | 5.0 |
| 5. Iron oxide red | 0.4 |
| 6. Iron oxide yellow | 2.0 |
| 7. Amber | 0.4 |
| 8. Iron oxide black | 0.1 |
| 9. Dimethylpolysiloxane (6 cs) | 7.0 |
| 10. Glyceryl trioctanoate | 1.5 |
| 11. Dipentaerythritol fatty acid ester | 1.5 |

[Preparation Process]

(A) The ingredients 1 to 8 were mixed together, and then ground to homogeneous powder A.
(B) The powder A was admixed with the ingredients 9 to 11, ground to homogeneous powder, and then compressed tightly into a metal pan.

In Table 2 shown hereinafter, the thus made face powder sample using the powders treated with Silicone 1 is referred to as Example 5, that using the powders treated with Silicone 2 as Example 6, that using the powders treated with KF99 as Comparative Example 1, and that using the powders treated with the alkoxy-modified silicone as Comparative Example 2.

By 50 female panelists, the face powder samples thus obtained were each examined for ease-of-use, makeup durability and resistance to pigment bleed by sebum and sweat, and these properties were evaluated in accordance with the criteria shown in Table 1.

TABLE 1

| Marks | Ease-of-use Makeup durability | Spread | Resistance to pigment bleed by sebum and sweat |
|---|---|---|---|
| 5 | good | light | good |
| 4 | fairly good | fairly light | Fairly good |
| 3 | average | average | average |
| 2 | rather bad | rather heavy | rather poor |
| 1 | bad | heavy | poor |

Judging from the average of marks given by the panelists, the quality of each face powder sample was assessed in accordance with the standards described below:

<Assessment Standards for Average Mark>

| Average mark obtained | Symbol (Quality) |
|---|---|
| 4.5 or above | ⊙ (good) |
| from 3.5 to lower than 4.5 | ○ (fairly good) |
| from 2.5 to lower than 3.5 | Δ (average) |
| from 1.5 to lower than 2.5 | X (rather bad) |
| lower than 1.5 | XX (bad) |

The evaluation results according to the aforementioned assessment standards are shown in Table 2.

TABLE 2

| | Example | | Comparative Example | |
|---|---|---|---|---|
| Item | 5 | 6 | 1 | 2 |
| Ease-of-use | ⊙ | ○ | Δ | Δ |
| Spread | ⊙ | ⊙ | ○ | Δ |
| Resistance to ooze of sebum and sweat | ○ | ⊙ | Δ | Δ |
| Makeup durability | ⊙ | ⊙ | ○~Δ | Δ~X |

As can be seen from Table 2, it has been demonstrated that the compressed face powders prepared in Examples 5 and 6 spread well and had satisfactory usability, high resistance to ooze of sebum and good makeup durability, compared with those prepared in Comparative Examples 1 and 2.

Further, the other powders treated with the present silicones in the manner described below were also used for preparing cosmetic materials in the following Examples 7 to 18 (excluding Examples 12 and 17):

In a reaction vessel, each of the powders previously heat-treated by drying under reduced pressure was placed in an amount of 98 parts by weight. Thereto, a toluene solution containing 2 parts by weight of the present silicone 1, 2, 3 or 4 was added gradually with stirring. Then, the temperature of the reaction vessel was raised to distill off the toluene. Further, the stirring was continued for 3 hours at 150° C. to effect the baking treatment. The thus treated powders were each cooled to room temperature in a stream of nitrogen, and used for preparing cosmetic material samples.

EXAMPLE 7

Eyeliner containing the following ingredients was prepared in accordance with the process described below:

| Ingredients | Amount mixed (%) |
|---|---|
| 1. Decamethylcyclopentasiloxane | 39.0 |
| 2. Polyether-modified siloxane (*1) | 3.0 |
| 3. Organic silicone resin (*2) | 15.0 |
| 4. Dioctadecyldimethylammonium salt-modified montmorillonite | 3.0 |
| 5. Iron oxide black treated with Silicone 1 | 10.0 |
| 6. 1,3-Butylene glycol | 5.0 |
| 7. Sodium dehydroacetate | proper |
| 8. Antiseptic | proper |
| 9. Perfume | proper |
| 10. Purified water | the rest |

(*1) KF-6017 (produced by Shin-Etsu Chemical Co., Ltd.)
(*2) 50% decamethylcyclopentasiloxane solution of netted silicone compound having a $[Me_3SiO_{1/2}]/[SiO_2]$ ratio of 0.8, KF7312J (produced by Shin-Etsu Chemical Co., Ltd.)

[Preparation Process]

A: The ingredients 1 to 4 were mixed together, and thereto the ingredient 5 was further added. These ingredients were dispersed homogeneously.

B: The ingredients 5, 7, 8 and 10 were mixed.

C: The mixture obtained in the step B was added little by little to the dispersion obtained in the step A to make an emulsion, and then the ingredient 9 was added to the emulsion.

The thus prepared eyeliner spread smoothly, and so the users thereof were able to outline the eyes easily. Further, this eyeliner had no tacky feel, but provided cool and dry feelings to the users. In addition, it was confirmed that the present eyeliner caused no change in quality by temperature and aging, it had very excellent usability and stability, and the duration of its effect was very long because of its high resistance to water, sweat and the like.

EXAMPLE 8

The following ingredients were mixed together, and made into foundation in accordance with the process described below:

| Ingredients | Amount mixed (%) |
| --- | --- |
| 1. Decamethylcyclopentasiloxane | 45.0 |
| 2. Dimethylpolysiloxane (6 cs) | 5.0 |
| 3. Polyether-modified siloxane (*1) | 2.0 |
| 4. Octadecyldimethylbenzylammonium salt-modified montmorillonite | 4.0 |
| 5. Titanium dioxide treated with Silicone 1 | 10.0 |
| 6. Talc treated with Silicone 1 | 6.0 |
| 7. Mica treated with Silicone 1 | 6.0 |
| 8. Iron oxide red treated with Silicone 1 | 1.6 |
| 9. Iron oxide yellow treated with Silicone 1 | 0.7 |
| 10. Iron oxide black treated with Silicone 1 | 0.2 |
| 11. Dipropylene glycol | 5.0 |
| 12. Methyl paraoxybenzoate | 0.3 |
| 13. 2-Amino-2-methyl-1,3-propanediol | 0.2 |
| 14. Hydrochloric acid | 0.1 |
| 15. Perfume | proper |
| 16. Water | the rest |

(*1) KF-6017 (produced by Shin-Etsu Chemical Co., Ltd.)

[Preparation Process]

A: The ingredients 1 to 5 were mixed together under heating, and thereto the ingredients 6 to 11 were added. Then, these mixed ingredients were made homogeneous.

B: The ingredients 12, 13, 14 and 16 were mixed together, and made into a solution by heating (the pH of this aqueous solution was 9.0).

C: The solution obtained in the step B was added little by little to the homogeneous dispersion obtained in the step A with stirring, thereby making an emulsion. After the emulsion was cooled, the ingredient 15 was added thereto.

The foundation thus prepared had fine texture, spread lightly and smoothly, had neither oily nor tacky feel, and rendered the skin moist, youthful and refreshing. Further, it was confirmed that the present foundation ensured durable makeup effect to the users, and besides, caused no change by fluctuation of temperature and passage of time, namely it had very high stability.

EXAMPLE 9

Eye shadow constituted of the following ingredients was prepared in accordance with the process described below:

| Ingredients | Amount mixed (%) |
| --- | --- |
| 1. Decamethylcyclopentasiloxane | 15.0 |
| 2. Dimethylpolysiloxane (6 cs) | 10.0 |
| 3. Organopolysiloxane modified with both polyoxyalkylene and alkyl groups (*1) | 2.0 |
| 4. PEG(10) lauryl ether (*2) | 0.5 |
| 5. Chromium oxide treated with Silicone 1 | 6.2 |
| 6. Ultramarine blue treated with Silicone 1 | 4.0 |
| 6. 1,3-Butylene glycol | 5.0 |
| 7. Titanium-coated mica treated with Silicone 1 | 6.0 |
| 8. Sodium chloride | 2.0 |
| 9. Propylene glycol | 8.0 |
| 10. Antiseptic | proper |
| 11. Perfume | proper |
| 12. Purified water | the rest |

(*1) KF6026 (produced by Shin-Etsu Chemical Co., Ltd.)
(*2) polyethylene glycol lauryl ether having 10 oxyethylene units.

[Preparation Process]

A: The ingredients 1 to 4 were mixed together, and thereto the ingredients 5 to 7 were further added. These ingredients were dispersed homogeneously.

B: The ingredients 8, 9, 10 and 12 were mixed to make a homogeneous solution.

C: The solution obtained in the step B was added little by little to the dispersion obtained in the step A with stirring, thereby making an emulsion, and then the ingredient 11 was added to the emulsion.

The thus prepared eye shadow spread lightly and smoothly, had neither oily nor powdery feel, and provided moist and refreshing feelings to the users. Further, it was confirmed that the present eye shadow ensured durable makeup effect to the users because of its high water-resistance, water repellency and sweat resistance, and besides, caused no change by fluctuation of temperature and passage of time, namely it had very high stability.

EXAMPLE 10

Eyeliner constituted of the following ingredients was repared in accordance with the process described below:

| Ingredients | Amount mixed (%) |
| --- | --- |
| 1. Decamethylcyclopentanesiloxane | 22.0 |
| 2. Dimethylpolysiloxane (6 cs) | 5.0 |
| 3. Jojoba oil | 2.0 |
| 4. Organopolysiloxane modified with both polyoxyalkylene and alkyl groups (*1) | 1.0 |
| 5. Iron oxide black treated with Silicone 4 | 20.0 |
| 6. Ethanol | 5.0 |
| 7. Antiseptic | proper |
| 8. Purified water | the rest |

(*1) KF6026 (produced by Shin-Etsu Chemical Co., Ltd.)

[Preparation Process]

A: The ingredients 1 to 4 were mixed together under heating, and thereto the ingredient 5 was further added. These ingredients were dispersed homogeneously.

B: The ingredients 6 to 8 were mixed and warmed to make a solution.

C: The solution obtained in the step B was added little by little to the dispersion obtained in the step A with stirring, thereby making an emulsion.

The thus prepared eyeliner spread smoothly, had neither oily nor powdery feel, and provided moist and refreshing feelings to the users. Further, it was confirmed that the present eyeliner ensured durable makeup effect to the users because of its high water-resistance, water repellency and sweat resistance, and besides, caused no change by fluctuation of temperature and passage of time, namely it had very high stability.

EXAMPLE 11

Liquid emulsive foundation constituted of the following ingredients was prepared in accordance with the process described below:

| Ingredients | Amount mixed (%) |
| --- | --- |
| 1. Dimethylpolysiloxane (6 cs) | 5.0 |
| 2. Decamethylcyclopentasiloxane | 15.0 |
| 3. Squalane | 4.0 |
| 4. Neopentyl glycol dioctanoate | 3.0 |
| 5. Miristic acid isostearic acid glyceride | 2.0 |
| 6. α-Monoisostearyl glyceryl ether | 1.0 |
| 7. Organopolysiloxane modified with both polyoxyalkylene and alkyl groups (*1) | 1.0 |
| 8. Aluminum distearate | 0.2 |
| 9. Titanium dioxide treated with Silicone 2 | 5.0 |
| 10. Sericite treated with Silicone 2 | 2.0 |
| 11. Talc treated with Silicone 2 | 3.0 |
| 12. Iron oxide red treated with Silicone 2 | 0.4 |
| 13. Iron oxide yellow treated with Silicone 2 | 0.7 |
| 14. Iron oxide black treated with Silicone 2 | 0.1 |
| 15. Magnesium sulfate | 0.7 |
| 16. Glycerin | 3.0 |
| 17. Antiseptic | proper |
| 18. Perfume | proper |
| 19. Purified water | the rest |

(*1) KF6026 (produced by Shin-Etsu Chemical Co., Ltd.)

[Preparation Process]

A: The ingredients 1 to 8 were mixed together under heating, and thereto the ingredients 9 to 14 were added. Then, these mixed ingredients were made homogeneous.

B: The ingredients 15, 16, 17 and 19 were mixed together, and made into a solution by heating.

C: The solution obtained in the step B was added little by little to the homogeneous dispersion obtained in the step A with stirring, thereby making an emulsion. After the emulsion was cooled, the ingredient 18 was added thereto.

The liquid emulsive foundation thus prepared had low viscosity and fine texture, spread smoothly, had neither tacky nor oily feel, and rendered the skin moist, youthful and refreshing. Further, it was confirmed that the present foundation ensured durable makeup effect to the users, and besides, caused no change by fluctuation of temperature and passage of time, namely it had very high stability.

EXAMPLE 12

Cream constituted of the following ingredients was prepared in accordance with the process described below:

| Ingredients | Amount mixed (%) |
| --- | --- |
| 1. Dimethylpolysiloxane (6 cs) | 6.0 |
| 2. Methylphenylpolysiloxane | 4.0 |
| 3. Squalane | 5.0 |
| 4. Neopentyl glycol dioctanoate | 3.0 |
| 5. Polyether-modified silicone (*1) | 3.0 |

-continued

| Ingredients | Amount mixed (%) |
| --- | --- |
| 6. Fine-grained titanium dioxide treated so as to have hydrophobility (*2) | 2.0 |
| 7. Magnesium sulfate | 0.7 |
| 8. Glycerin | 10.0 |
| 9. Antiseptic | proper |
| 10. Perfume | proper |
| 11. Purified water | the rest |

(*1) KF6012 (produced by Shin-Etsu Chemical Co., Ltd.).
(*2) The ingredient 6 was prepared as follows: Fine-grained titanium dioxide having an average grain size of 0.05 μm was dispersed into water in a concentration of 10 weight %. Thereto was added a 10 weight % sodium silicate solution (SiO$_2$/Na$_2$O ratio: 0.5 by mole) in a proportion of 2 weight % based on the SiO$_2$ to the titanium dioxide. This admixture was stirred thoroughly. Thereafter, a 10 weight % aluminum sulfate solution in anamount corresponding to the proportion of 7.5 weight % based on the Al$_2$O$_3$ to the titanium dioxide was added gradually to the foregoing admixture, thereby depositing hydrated silicate and hydrated alumina on the grain surface of titanium dioxide. After the conclusion of the reaction, the products were filtered off, washed, dried and the ground with a jet mill. The ground products were transferred into a Henschel mixer, and thereto 2 weight % ofSilicone 2 was added with thorough stirring, followed by baking treatment at 120° C.

[Preparation Process]

A: The ingredients 1 to 5 were mixed together under heating, and therein the ingredient 6 was admixed homogeneously.

B: The ingredients 7, 8, 9 and 11 were mixed together under heating to make a solution.

C: The solution obtained in the step B was added gradually to the mixture obtained in the step A with stirring to make an emulsion. After cooling the emulsion, the ingredient 10 was added to prepare cream.

The thus prepared cream had fine texture, spread smoothly, had neither tacky nor oily feel, and rendered the skin moist, youthful and refreshing. Further, it was confirmed that the present cream ensured durable makeup effect to the users, and besides, caused no change by fluctuation of temperature and passage of time, namely it had very high stability.

EXAMPLE 13

Sun screening milky lotion constituted of the following ingredients was prepared in accordance with the process described below:

| Ingredients | Amount mixed (%) |
| --- | --- |
| 1. Decamethylcyclopentasiloxane | 20.0 |
| 2. Methylphenylpolysiloxane | 3.0 |
| 3. Sorbitan monoisostearate | 1.0 |
| 4. Polyether-modified silicone (*1) | 0.5 |
| 5. Trimethylsiloxysilicate | 1.0 |
| 6. Octyl paramethoxycinnamate | 4.0 |
| 7. Fine-grained titanium oxide treated with Silicone 2 | 8.0 |
| 8. Sorbitol | 2.0 |
| 9. Sodium chloride | 2.0 |
| 10. Antiseptic | proper |
| 11. Perfume | proper |
| 12. Purified water | the rest |

(*1) KF6015 (produced by Shin-Etsu Chemical Co., Ltd.)

[Preparation Process]

A: The ingredients 1 to 6 were mixed together under heating, and therein the ingredient 7 was dispersed homogeneously.

B: The ingredients 8, 9, 10 and 12 was mixed together under heating.

C: The solution obtained in the step B was added gradually to the dispersion obtained in the step A with stirring to make an emulsion. After cooling the emulsion, the ingredient 11 was added to prepare sunscreening milky lotion.

The thus prepared milky lotion had fine texture, spread smoothly, had no tacky feel, and rendered the skin moist and youthful. Further, it was confirmed that the present milky lotion ensured durable makeup effect and lasting UV screening effect to the users, and besides, caused no change by fluctuation of temperature and passage of time, namely it had very high stability.

EXAMPLE 14

Liquid foundation constituted of the following ingredients was prepared in accordance with the process described below:

| Ingredients | Amount mixed (%) |
| --- | --- |
| 1. Decamethylcyclopentasiloxane | 6.0 |
| 2. Dimethylpolysiloxane (6 cs) | 8.0 |
| 3. Octyl paramethoxycinnamate | 3.0 |
| 4. 12-Hydroxystearic acid | 1.0 |
| 5. Fluorine-modified silicone (*1) | 15.0 |
| 6. Polyether-modified silicone (*2) | 5.0 |
| 7. Spherical silicone resin powder (*3) | 3.0 |
| 8. Fine-grained titanium dioxide treated with Silicone 3 | 8.0 |
| 9. Mica treated with Silicone 3 | 1.0 |
| 10. Titanium dioxide treated with silicone 3 | 5.0 |
| 11. Iron oxide red treated with Silicone 3 | 0.9 |
| 12. Iron oxide yellow treated with Silicone 3 | 2.0 |
| 13. Iron oxide black treated with Silicone 3 | 1.0 |
| 14. Ethanol | 15.0 |
| 15. Glycerin | 3.0 |
| 16. Magnesium sulfate | 1.0 |
| 17. Antiseptic | proper |
| 18. Perfume | proper |
| 19. Water | the rest |

(*1) FL-100 (produced by Shin-Etsu Chemical Co., Ltd.)
(*2) Silicone modified with both polyoxyethylene and trifluoropropyl groups
(*3) KMP590 (produced by Shin-Etsu Chemical Co., Ltd.)

[Preparation Process]
A: The ingredients 7 to 13 were mixed homogeneously.
B: The ingredients 1 to 6 were heated at 70° C. and mixed together. The mixture obtained was added to the mixture obtained in the step A to make a homogeneous dispersion.
C: The ingredients 14, 15, 16, 17 and 19 were warmed to 40° C., and added little by little to the homogeneous dispersion obtained in the step B to make an emulsion. After the emulsion was cooled, the ingredient 18 was added thereto.

The liquid foundation thus prepared had no tacky feel, spread smoothly, and gave highly refreshing feeling to the skin. Further, it was confirmed that the present foundation caused no change by fluctuation of temperature and passage of time, namely it had very high stability.

EXAMPLE 15

Eyeliner constituted of the following ingredients was prepared in accordance with the process described below:

| Ingredients | Amount mixed (%) |
| --- | --- |
| 1. Decamethylcyclopentanesiloxane | 22.0 |
| 2. Dimethylpolysiloxane (6 cs) | 5.0 |
| 3. Iron oxide black treated with Silicone 1 | 20.0 |
| 4. Vitamin E acetate | 0.2 |
| 5. Jojoba oil | 2.0 |
| 6. Bentonite | 3.0 |
| 7. Polyether-modified silicone (*1) | 2.0 |
| 8. Ethanol | 10.0 |
| 9. 1,3-Butylene glycol | 10.0 |
| 10. Antiseptic | proper |
| 11. Perfume | proper |
| 12. Purified water | the rest |

(*1) KF6017 (produced by Shin-Etsu Chemical Co., Ltd.)

[Preparation Process]
A: The ingredients 1 and 2 were mixed with the ingredients 4 to 7, and therein the ingredient 3 was further mixed and dispersed homogeneously.
B: The ingredients 8, 9, 10 and 12 were mixed together.
C: The mixture obtained in the step B was added little by little to the dispersion obtained in the step A to make an emulsion. After cooling the emulsion, the ingredient 11 was added thereto.

The thus prepared eyeliner spread smoothly, and so the users thereof were able to outline the eyes easily. Further, this eyeliner had no tacky feel, but provided cool and dry feelings to the users. In addition, it was confirmed that the present eyeliner caused no change in quality by temperature and aging, it had very excellent usability and stability, and the duration of its effect was very long because of its high resistance to water, sweat and the like.

EXAMPLE 16

Cream constituted of the following ingredients was prepared in accordance with the process described below:

| Ingredients | Amount mixed (%) |
| --- | --- |
| 1. Decamethylcyclopentasiloxane | 16.0 |
| 2. Dimethylpolysiloxane (6 cs) | 4.0 |
| 3. Polyether-modified silicone (*1) | 5.0 |
| 4. POE(5) octyl dodecyl ether | 1.0 |
| 5. Polyoxyethylenesorbitan (20 E.O.) monostearic acid ester | 0.5 |
| 6. Zinc oxide treated with silica (*2) | 2.0 |
| 7. Fine-grained titanium dioxide treated with Silicone 4 | 10.0 |
| 8. Liquid paraffin | 2.0 |
| 9. Macadamia nut oil | 1.0 |
| 10. Scutellariae radix extract (*3) | 1.0 |
| 11. Gentian root extract (*4) | 0.5 |
| 12. Ethanol | 5.0 |
| 13. 1,3-Butylene glycol | 2.0 |
| 14. Antiseptic | proper |
| 15. Perfume | proper |
| 16. Purified water | the rest |

(*1) KF6017 (produced by Shin-Etsu Chemical Co., Ltd.)
(*2) Silica having grain sizes of from 0.01 to 10 μm wherein zinc oxide is encapsulated in a proportion of 50%; SUNSPHERE SZ-5 (trade name, a product of ASAHI GLASS Co., LTD.)
(*3) Essence extracted with 50% 1,3-butylene glycol water
(*4) Essence extracted with 20% ethanol water

[Preparation Process]
A: The ingredients 6 to 9 were mixed to make a dispersion.
B: The ingredients 1 to 5 were mixed, and thereto the dispersion obtained in the step A was added.
C: The ingredients 10 to 14 were mixed with the ingredient 16, and thereto the mixture obtained in the step B was added to make an emulsion.

D: After the emulsion was cooled, the ingredient 15 was added thereto.

The thus prepared cream had no tacky feel, not only spread smoothly but also provided clingy feeling and fitted in with the skin, and further ensured lustrous finish and durable makeup effects. In addition, it was confirmed that the present cream caused no change by fluctuation of temperature and passage of time, namely it had very high stability.

EXAMPLE 17

Foundation constituted of the following ingredients was prepared in accordance with the process described below:

| Ingredients | Amount mixed (%) |
| --- | --- |
| 1. Decamethylcyclopentasiloxane | 27.0 |
| 2. Methylphenylpolysiloxane | 3.0 |
| 3. Glyceryl triisooctanoate | 10.0 |
| 4. Polyether-modified silicone (*1) | 1.0 |
| 5. Polyglyceryl monoisostearate | 3.0 |
| 6. Mixed powder treated so as to have hydrophobity (*2) | 18.0 |
| 7. Iron oxide red | 1.2 |
| 8. Iron oxide yellow | 2.6 |
| 9. Iron oxide black | 0.2 |
| 10. 1,3-Butylene glycol | 7.0 |
| 11. Sodium chloride | 0.5 |
| 12. Antiseptic | proper |
| 13. Perfume | proper |
| 14. Purified water | the rest |

(*1) Organopolysiloxanes modified with both polyoxyalkylene and alkyl groups; KF6026 (trade name, a product of Shin-Etsu chemical Co., Ltd.)
(*2) The mixed powder is a mixture of (a) fine-grained titanium oxide, (b) fine-grained zinc oxide, (c) talc and (d) mica.

[Preparation Process]

A: The powders (a) to (d) were mixed, and thereto Silicone 2 was added in a proportion of 2 weight %, followed by heat treatment.

B: The ingredients 1 to 5 were mixed and dissolved under heating. Therein, the ingredient 6 (obtained in the step A) and the ingredients 7 to 9 were dispersed homogeneously.

C: The ingredients 10 to 12 were mixed with the ingredient 14, and then added to the dispersion obtained in the step B, followed by emulsifying treatment.

D: After the emulsion obtained in the step C was cooled, the ingredient 13 was added thereto.

The thus prepared foundation had no tacky feel, not only spread smoothly but also provided clingy feeling and fitted in with the skin, and further had lustrous finish and durable makeup effects. In addition, it was confirmed that the present foundation caused no-change by fluctuation of temperature and passage of time, namely it had very high stability.

EXAMPLE 18

Sun protect cream constituted of the following ingredients was prepared in accordance with the process described below:

| Ingredients | Amount mixed (%) |
| --- | --- |
| 1. Decamethylcyclopentasiloxane | 17.5 |
| 2. KP545 (*1) | 12.0 |
| 3. Glyceryl triisooctanoate | 5.0 |
| 4. Octyl paramethoxycinnamate | 6.0 |

-continued

| Ingredients | Amount mixed (%) |
| --- | --- |
| 5. KSG21 (*2) | 5.0 |
| 6. Polyether-modified silicone (*3) | 1.0 |
| 7. Zinc oxide treated with Silicone 4 | 20.0 |
| 8. Sodium chloride | 0.5 |
| 9. 1,3-Butylene glycol | 2.0 |
| 10. Antiseptic | proper |
| 11. Perfume | proper |
| 12. Purified water | the rest |

(*1) Acrylsilicone produced by Shin-Etsu chemical Co., Ltd.
(*2) Silicone gel produced by Shin-Etsu chemical Co., Ltd.
(*3) Organopolysiloxanes modified with both polyoxyalkylene and alkyl groups, KF6026 (trade name, a product of Shin-Etsu chemical Co., Ltd.)

[Preparation Process]

A: The ingredient 2 was added to a part of the ingredient 1, and these ingredients were homogenized. Therein, the ingredient 7 was admixed, and dispersed by means of a beads mill.

B: The rest of the ingredient 1 and the ingredients 3 to 6 were mixed together to make a homogeneous mixture.

C: The ingredients 8 to 10 were mixed and dissolved in the ingredient 12.

D: The mixture obtained in the step B was added to the solution obtained in the step C, followed by emulsifying treatment. To the emulsion obtained, the dispersion obtained in the step A and the ingredient 11 were further added.

The thus prepared sun protect cream had no tacky feel, not only spread smoothly but also provided clingy feeling and fitted in with the skin, and further ensured lustrous finish and durable makeup effects. In addition, it was confirmed that the present cream caused no change by fluctuation of temperature and passage of time, namely it had very high stability.

ADVANTAGES OF THE INVENTION

When the cosmetics in which the powder(s) surface-treated with the present silicone compounds represented by formula (1) are mixed are put on the skin, they spread smoothly, havenooily feel, and rendertheskinmoist, freshandyouthful. Further, they provide a refreshed feel and durable makeup effect to the users, and besides, cause no change by fluctuation of temperature and passage of time, namely they have very high stability.

What is claimed is:

1. A non-cross linked silicone for powder treatment, being represented by formula (1):

$$R^1{}_a R^2{}_b R^3{}_c SiO_{(4-a-b-c)/2} \qquad (1)$$

wherein

R$^1$ groups, which are the same or different, each represent an organic group selected from alkyl groups containing 1 to 30 carbon atoms, aryl groups, aralkyl groups, fluorinated alkyl groups and organic groups represented by formula (2);

R$^2$ groups each represent a reactive substituent selected from a hydrogen atom, a hydroxyl group and alkoxy groups containing 1 to 6 carbon atoms, wherein said reactive substituent is attached to a silicon atom in the siloxane chain directly or via a linkage group comprising at least one carbon, oxygen or silicon atom;

$R^3$ groups each represent a silicone compound residue represented by formula (3);

a is a number of from 1.0 to 2.5;
b is a number of from 0.001 to 1.5; and
c is a number of from 0.001 to 1.5;

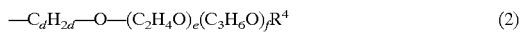

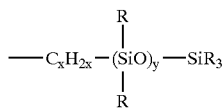

wherein
R is in each case independently a 1–30C alkyl group, an aryl group, or a fluorinated alkyl group;
$R^4$ is a hydrocarbon group containing 4 to 30 carbon atoms or an organic group represented by $R^5$—(CO)—;
$R^5$ is a hydrocarbon group containing 1 to 30 carbon atoms;
d is an integer of from 0 to 15;
e is an integer of from 0 to 50;
f is an integer of from 0 to 50;
x is an integer of from 1 to 5; and
y is an integer of from 0 to 500.

2. A surface-treated powder composition comprising a powder and a silicone according to claim 1, wherein said composition contains 0.1 to 30 parts by weight of said silicone per 100 parts by weight of said powder, wherein said silicone is adhered to the surface of said powder.

3. A surface-treated powder composition according to claim 2, wherein said powder is a zinc oxide powder.

4. A surface-treated powder composition according to claim 2, wherein said powder is a titanium dioxide powder.

5. A surface-treated powder composition according to claim 2, wherein said powder is an extender pigment.

6. A surface-treated powder composition according to claim 5, wherein the extender pigment is mica.

7. A surface-treated powder composition according to claim 5, wherein the extender pigment is sericite.

8. A cosmetic material comprising a mixture of powders wherein at least one of said powders is a surface-treated powder composition according to claim 2.

9. A cosmetic material according to claim 8, further comprising at least one unctuous agent.

10. A cosmetic material according to claim 9, wherein said at least one unctuous agent is an oil.

11. A cosmetic material according to claim 9, wherein at least one unctuous agent is a silicone oil containing a volatile silicone, an organosiloxane, a cyclic siloxane, a silicone rubber, or a mixture thereof.

12. A cosmetic material according to claim 9, wherein at least one unctuous agent is a fluorine-containing oil, or an oil having amino groups.

13. A cosmetic material according to claim 8, further comprising a surfactant as a constituent.

14. A cosmetic material according to claim 13, wherein the surfactant is a polyoxyalkylene organopolysiloxane.

15. A cosmetic material according to claim 14, wherein the modified silicone is a silicone having an HLB value of 2 to 8.

16. A cosmetic material according to claim 8, further comprising a powdered coloring material.

17. A cosmetic material according to claim 16, further comprising a silicone resin powder, or a powder having a silicone elastomer as its skeleton, or a mixture thereof.

18. A cosmetic material according to claim 8, further comprising water as a constituent.

19. A cosmetic material according to claim 8, further comprising as a constituent a compound having a hydroxyl group in its molecular structure.

20. A cosmetic material according to claim 19, wherein the compound having a hydroxyl group in its molecular structure is a monohydric water-soluble alcohol, a polyhydric water-soluble alcohol or a mixture thereof.

21. A cosmetic material according to claim 19, wherein the compound having a hydroxyl group in its molecular structure is a water-soluble polymer.

22. A cosmetic material according to claim 8, further comprising cross-linked organopolysiloxanes as a constituent.

23. A cosmetic material according to claim 22, wherein the cross-linked organopolysiloxanes are cross-linked organopolysiloxanes which cause swelling when they contain a silicone having low viscosity of from 0.65 to 10.0 $mm^2$/sec at 25° C. in a quantity larger than the weight of the cross-linked organopolysiloxanes themselves.

24. A cosmetic material according to claim 22, wherein the cross-linked organopolysiloxanes are organopolysiloxanes having a cross-linked structure formed by the reaction between hydrogen atoms bonded directly to silicon atoms and a cross-linking agent having at least two vinylic reactive moieties per molecular.

25. A cosmetic material according to claim 22, wherein the cross-linked organopolysiloxanes are organopolysiloxanes having in their cross-links at least one kind of moiety selected from polyoxyalkylene, alkyl, alkenyl, aryl and fluoroalkyl moieties.

26. A cosmetic material according to claim 8, further comprising silicone resin as a constituent.

27. A cosmetic material according to claim 26, wherein the silicone resin is an acrylsilicone resin.

28. A cosmetic material according to claim 27, wherein the acrylsilicone resin is an acrylsilicone resin containing at least one moiety selected from pyrrolidone, alkyl, polyoxyalkylene and fluoroalkyl moieties.

29. A cosmetic material according to claim 26, wherein the silicone resin is a silicone compound having a network structure.

30. A cosmetic material according to claim 29, wherein the silicone compound having network structure is a netted silicone compound containing at least one moiety selected from the group consisting of pyrrolidone, long-chain alkyl, polyoxyalkylene, fluoroalkyl and amino moieties.

31. A skincare cosmetic material comprising a cosmetic material according to claim 8.

32. A hair-care cosmetic material comprising a cosmetic material according to claim 8.

33. An antiperspirant cosmetic material comprising a cosmetic material according to claim 8.

34. A makeup cosmetic material comprising a cosmetic material according to claim 8.

35. An UV protective cosmetic material comprising a cosmetic material according to claim 8.

36. In a cosmetic composition comprising a cosmetic material which composition is in the form of a liquid, emulsion, cream, solid, paste, gel, mousse or spray, the improvement wherein the cosmetic material is one according to claim 8.

37. A silicone according to claim 1, wherein $R^1$ is methyl, ethyl, propyl, butyl, pentyl, hexyl, heptyl, octyl, nonyl, decyl, cyclopentyl, cyclohexyl, phenyl, tolyl, benzyl, phenethyl, trifluoropropyl or heptadecafluorodecyl.

38. A silicone according to claim 1, wherein $R^2$ is an alkoxy group containing 1 to 3 carbon atoms.

39. A silicone according to claim 1 that is

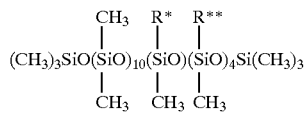

wherein

R* is —C2H4Si(OEt)3, and

R** is

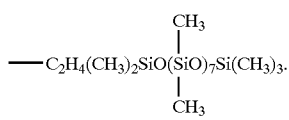

40. A cosmetic material according to claim 8, wherein said material comprises carnauba wax, fatty acid soap, iron oxide, titanium dioxide, sorbitol, acryl-silicone resin, or a mixture thereof.

41. A cosmetic material according to claim 8, wherein said material comprises carnauba wax, fatty acid soap, iron oxide, titanium dioxide, sorbitol, acryl-silicone resin, cross-linked organopolysiloxane which causes swelling when it contains a silicone having low viscosity of 0.65 to 10.0 $mm^2/sec(25°$ C.) in a quantity larger than its self weight, or a mixture thereof, and wherein the surface-treated powder is zinc oxide, and wherein the silicone used for treating the surface of the powder is

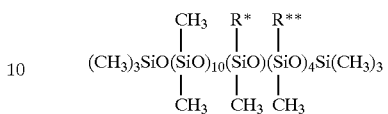

wherein

R* is —C2H4Si(OEt)3, and

R** is

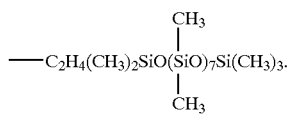

* * * * *